United States Patent
Rudloff et al.

(10) Patent No.: US 7,164,031 B2
(45) Date of Patent: Jan. 16, 2007

(54) METHOD FOR THE PRODUCTION OF 2-PYRROLIDONE

(75) Inventors: Martin Rudloff, Weisenheim (DE); Peter Stops, Altrip (DE); Erhard Henkes, Einhausen (DE); Helmut Schmidtke, Bensheim (DE); Rolf-Hartmuth Fischer, Heidelberg (DE); Manfred Julius, Limburgerhof (DE); Rolf Lebkücher, Mannheim (DE); Karl-Heinz Ross, Grünstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 316 days.

(21) Appl. No.: 10/487,452

(22) PCT Filed: Aug. 30, 2002

(86) PCT No.: PCT/EP02/09721

§ 371 (c)(1),
(2), (4) Date: Feb. 24, 2004

(87) PCT Pub. No.: WO03/022811

PCT Pub. Date: Mar. 20, 2003

(65) Prior Publication Data

US 2004/0242900 A1 Dec. 2, 2004

(30) Foreign Application Priority Data

Sep. 7, 2001 (DE) ............................ 101 43 824

(51) Int. Cl.
*C07D 207/267* (2006.01)
(52) U.S. Cl. ..................................................... 548/552
(58) Field of Classification Search ................. 548/552
See application file for complete search history.

(56) References Cited

U.S. PATENT DOCUMENTS

| 3,133,085 A | 5/1964 | Start et al. |
| 3,975,400 A | 8/1976 | Mimmele et al. |
| 4,014,900 A | 3/1977 | Pusztaszeri |
| 4,824,967 A | 4/1989 | Liu et al. |
| 5,393,888 A | 2/1995 | Minnock et al. |

FOREIGN PATENT DOCUMENTS

| DE | 1795507 | 1/1972 |
| WO | 99/52866 | 10/1999 |

OTHER PUBLICATIONS

Ullmann's Encyclopedia of Ind.Chem, 5th Ed., vol. A22, 457-463.
Chemische Berichte 69, 2727-31, 1936.
Chem. Abst.93 (19): 186154b.
Der.Abst.No. 95-176475/23.

*Primary Examiner*—Joseph K. McKane
*Assistant Examiner*—Robert Shiao
(74) *Attorney, Agent, or Firm*—Novak Druce & Quigg, LLP

(57) ABSTRACT

A process for continuously preparing 2-pyrrolidone by reacting gamma-butyrolactone with ammonia in the liquid phase in the presence of water, wherein the reaction is carried out at a temperature of from 275 to 300° C. and an absolute pressure of from 140 to 180 bar.

14 Claims, No Drawings

METHOD FOR THE PRODUCTION OF 2-PYRROLIDONE

The present invention relates to a process for continuously preparing 2-pyrrolidone by reacting gamma-butyrolactone with ammonia in the liquid phase in the presence of water.

2-Pyrrolidone (gamma-butyrolactam) is an important solvent, extractant and intermediate for preparing N-vinylpyrrolidone and pharmaceuticals (Ullmann's Encyclopedia of Industrial Chemistry, 5$^{th}$ Ed., Vol. A22, pages 457 to 463).

In Chemische Berichte 69, page 2727–31, 1936, the batchwise reaction of GBL with anhydrous ammonia at 200° C. under autogenous pressure is described. The reaction affords 2-pyrrolidone in a yield of 64%.

U.S. Pat. No. 4,824,967 (GAF Corp.) describes the synthesis of 2-pyrrolidone by reacting gamma-butyrolactone (GBL) with ammonia in the gas phase over a magnesium silicate catalyst at from 230 to 300° C., preferably from 250 to 290° C., and a pressure of from 50 to 300 psig (3.5 to 20.7 bar).

Chem. Abstracts 93(19): 186154b (RO-A-75-82714, Combanitul Petrochimic)-describes the batchwise reaction of GBL with ammonia in a molar ratio of from 1:1.1 to 1:1.2 at from 270 to 330° C. and from 70 to 150 atm (70.9 to 152.0 bar).

DE-A-17 95 007 (BASF AG) describes a continuous process for preparing 2-pyrrolidone from GBL and ammonia in the liquid phase, in which the reaction at temperatures between 180 and 340° C. and a pressure which is at least 10%, preferably at least 20%, above the autogenous pressure of the reaction mixture at reaction temperature.

The reaction pressures are generally between 25 and 280 at., preferably between 45 and 130 at. (1 atmosphere=1.01325 bar). The reaction temperatures are preferably from 190 to 290° C. The inventive examples of DE-A-17 95 007 were carried out at 270° C., a pressure of from 70 to 200 at., and molar GBL:ammonia:water ratios of 1:5.6:2.4 (Example 1), 1:5.3:2.4 (Example 2) and 1:5.4:4.8 (Example 3).

Derwent Abstract No. 95-176475/23 (RO-B1-108 561, SC Chimcomplex SA) describes the continuous preparation of 2-pyrrolidone by reacting GBL with aqueous ammonia in the liquid phase in two stages, in which the first stage is carried out at from 40 to 45° C. and 1 atm and the second stage at from 270 to 280° C. and from 80 to 90 bar.

U.S. Pat. No. 5,393,888 (ISP Investments Inc.) describes the reaction of GBL with ammonia to give 2-pyrrolidone at molar GBL:ammonia ratios of 1:0.5 to 0.85, temperatures of from 200 to 375° C. and pressures of from 700 to 1800 psi (48.3 to 124.1 bar).

WO 99/52866 (Pantochim) discloses a process for continuously preparing 2-pyrrolidone by reacting GBL with ammonia in the liquid phase in three successive reaction stages, of which the first stage is operated at temperatures between 130 and 200° C., the second stage at temperatures between 200 and 250° C. and the third stage at temperatures between 250 and 320° C. The pressure in all three stages is between 40 and 120 ATE (40.53 and 121.59 bar), preferably between 60 and 100 ATE (60.80 and 101.33 bar).

U.S. Pat. No. 4,014,900 (S. F. Pusztaszeri) relates to a process for purifying commercial 2-pyrrolidone by treating with a metal hydroxide and flash evaporation from a heated surface at certain temperatures and pressures.

This invention includes the recognition that the prior art results, inter alia, in the following disadvantages:

a) the low space-time yield and a necessity of catalyst when carrying out the reaction in the gas phase, b) the large molar excess of ammonia based on GBL, which causes a high degree of technical complication in the workup of the reaction mixture and recovery of the unconverted ammonia and therefore high capital and energy costs in the method of DE-A-17 95 007 and c) the high degree of technical complexity coupled with high capital and operation costs when carrying out the reaction in a plurality of reaction stages, for example in accordance with WO 99/52866.

It is an object of the present invention to overcome the disadvantages of the prior art and to provide an improved, selective process for preparing 2-pyrrolidone in high yields and space-time yields and high quality (for example purity>99.5 GC area %, APHA color number≦30).

We have found that this object is achieved by a process for continuously preparing 2-pyrrolidone by reacting gamma-butyrolactone with ammonia in the liquid phase in the presence of water, which comprises carrying out the reaction at a temperature of from 275 to 300° C. and an absolute pressure of from 140 to 180 bar.

Preference is given to carrying out the process according to the invention at a temperature of from 280 to 295° C., in particular at a temperature of from 280 to 290° C., very particularly at a temperature of from 282 to 288° C., for example 285° C.

Preference is given to carrying out the reaction according to the invention at an absolute pressure of from 150 to 170 bar, in particular at an absolute pressure of from 155 to 165 bar, for example 160 bar.

The molar ratio of the starting materials, GBL:ammonia:water, in the process according to the invention is generally 1:(1.5 to 5):(0.5 to 4), preferably 1:(2 to 4):(1 to 3), in particular 1:(2.1 to 3.5):(1.5 to 2.8), very particularly 1:(2.2 to 3):(1.6 to 2.3), for example 1:2.6:1.9.

The process according to the invention can be performed, for example, as follows:

The reactor used is preferably a vertical, slender high-pressure tube which is equipped at its upper end with a decompression valve controlled via a pressure regulator. The feed streams are preferably preheated by the reactor effluent, so that the reaction temperatures according to the invention can be set in the reactor by the exothermicity. In the reactor, preference is given to installing a plurality of sieve trays to prevent backmixing and for better formation of a plug flow (like a stirred tank battery). The number of sieve trays may be from 10 to 30, preferably from 12 to 24.

Liquid ammonia, optionally mixed with recovered ammonia from the workup (see below), is conveyed with a pump, for example membrane pump, to a vapor-operated heater W1.

Water, optionally mixed with recovered water from the workup (see below), is likewise conveyed with a pump, for example piston pump, to a heater W1.

The liquid ammonia/water mixture is conducted from W1 via heat exchanger W3 to the lower end of the tubular reactor (preferred liquid phase mode).

GBL is conducted with a pump, for example membrane pump, through a vapor-operated heater W2, likewise at the lower end of the tubular reactor, where mixing of the starting materials takes place and the starting materials, GBL, ammonia and water, are present in the abovementioned molar ratio according to the invention.

In a particularly preferred embodiment, the GBL, and also the ammonia/water mixture are fed separately to the tubular reactor in the center of the reactor bottom through a two-material injector. While the GBL is introduced through the central nozzle at a high flow rate (preferably 4–12 ml/s), the ammonia/water mixture reaches the exterior of this nozzle through an annular gap in the reactor. The reactants are passed as a driving jet into a circular tube which is disposed in the inlet region of the reactor, encloses approx. one third of the free reactor cross section and has a length of preferably from 1.5 to 2.0 m. The recirculation of liquid, which is effected at the exterior of the circulation tube and is maintained by the driving jet, leads to intensive first contact of the reaction partners in the abovementioned, inventive molar ratio.

In the reactor, under the above-specified temperatures and pressures, the continuous reaction of GBL with ammonia proceeds in the liquid phase, in the presence of water and in an exothermic reaction to give 2-pyrrolidone.

The reaction is preferably carried out in the absence of a catalyst.

The average residence times of the reaction mixture in the reactor, determined with the density of GBL, ammonia (liquid) and water at ambient temperature (20° C.), depending on the loading, are generally from 20 to 60 min, preferably from 30 to 45 min.

The resulting reaction product is continuously decompressed out of the reactor to a distillation column K1 by initially passing the reactor effluent fully or partly through the heat exchanger W3 (see above) for heating the ammonia/water mixture and thus cooling it.

The excess ammonia is distilled off in the distillation column K1, for example at from 40 to 160° C. and from 15 to 18 bar, the heat being supplied by a circulation evaporator, and can be recycled into the synthesis.

Preference is given to distilling off the ammonia in this distillation stage in the presence of from 0.1 to 1% by weight, in particular from 0.5 to 0.9% by weight (based in each case on the amount of 2-pyrrolidone in the feed of this distillation stage) of hydroxides of the metals Na, K, Li, Ba or Ca.

Particular preference is given to distilling off the ammonia in this distillation stage in the presence of NaOH, which is metered into the bottom of this column by means of a pump as sodium hydroxide solution. For example, aqueous 25% sodium hydroxide solution is used here in such a way that the concentration of NaOH is from 0.1 to 1% by weight, in particular from 0.5 to 0.9% by weight (based in each case on the amount of 2-pyrrolidone in the feed of this distillation stage).

This invention includes the recognition that this particular process configuration binds $CO_2$ present in the reaction product, suppresses carbamate and carbaminate formation in the top of the column K1 and converts residual traces of unconverted GBL to the corresponding metal salt of gamma-hydroxybutyric acid, so that particularly pure 2-pyrrolidone is finally obtained.

Subsequently, the ammonia-free liquid phase is decompressed in a further distillation column where the water is distilled off, for example, at from 0.1 to 0.3 bar, in particular from 0.15 to 0.2 bar, and may be partly recycled into the synthesis. The heat may also be supplied here with a circulation evaporator.

The crude 2-pyrrolidone obtained in this way in the bottom of this column, which may contain small amounts of gamma-(N-2-pyrrolidinyl)butyramide and gamma-(N-2-pyrrolidinyl)butyric acid by-products, is then distilled to purity in a further distillation column, for example at pressures of from 1 to 2 mbar. (Boiling point of 2-pyrrolidone: 250° C./1013 mbar.)

In the process according to the invention, 2-pyrrolidone is obtained in yields of>93%, in particular>94%. The conversion of GBL is generally>98%, in particular>99%, very particularly>99.9%. The selectivity (based on GBL) is generally>93%, in particular>94%.

The 2-pyrrolidone obtained in accordance with the invention has a very high quality:

The purity is generally>99.5 GC area %, in particular≧99.8 GC area % (GC conditions: 25 m CP-WAX 52 CB, temperature program: 140° C./8 min. hold time, 5° C./min. heating rate, 180° C. end temperature/15 min. hold time). The content of 1,4-butanediol is generally<0.1 GC area %, in particular<0.07 GC area %, the content of GBL<0.1 GC area %, in particular<0.05 GC area % (GC conditions as above). The content of 3- and 4-methyl-2-pyrrolidone is generally in each case<0.1 GC area %, in particular in each case<0.08 GC area % (GC conditions as above).

The APHA color number of DIN ISO 6271 of the 2-pyrrolidone obtained in accordance with the invention is generally≦30, in particular<5.

The process according to the invention can also be performed in an apparatus as described in the document DE-A-17 95 007, it is explicitly incorporated herein by way of reference.

Preference is given to carrying out the process according to the invention in one stage, i.e. in one reactor.

In a particular embodiment of the process, a plurality of tubular reactors (for example two or three reactors, each as described above) in liquid phase mode may be connected in series, in which case the conditions in at least one of these reactors, preferably in the last of these reactors, are the reaction conditions according to the invention.

An example of such a series connection of reactors can be found in the documents WO 99/52866 (see FIG. 1 there, reactors no. 5, 9 and 13 and the description), which is explicitly incorporated herein by way of reference.

EXAMPLES

Example 1

The 2-pyrrolidone synthesis was carried out under the conditions specified below in continuous mode in a 1 l reactor (RA4, length x internal diameter=2000 mm×30 mm, annular gap 9 mm, volume=1.1 l, electrically heated). The reactor was operated in liquid phase mode in straight paths. Ammonia and water (as a mixture) and also GBL, were preheated and conveyed by means of pumps to the reactor inlet, where the two streams were mixed.

At the reactor outlet was disposed a high-pressure separator from which the gas phase (nitrogen and inerts) was decompressed as offgas. The liquid phase which separated was decompressed to atmospheric pressure in a vessel, and the ammonia which was used in excess and remained after the reaction evaporated off.

| | |
|---|---|
| Temperature: | 285° C. |
| Pressure: | 160 bar |
| | (pressure maintained by $N_2$) |
| Hourly space velocity: | 0.74 kg of GBL/($1_{Reactor}$*h) |
| Molar GBL:$NH_3$:$H_2O$ ratio | 1:2.6:1.9 |
| Offgas | 20 l (STP)/h |

[l (STP) = liters at STP = volume converted to standard conditions; reactor hourly space velocity in kg of GBL per liter of reactor volume and hour].

The table which follows lists the composition of the reaction effluents (after ammonia evaporation).

TABLE

GC analysis of the crude effluents
from the 2-pyrrolidone synthesis

| Experiment No. | 2-Pyrrolidone [GC area %] | GBL [GC area %] | Amide *) [GC area %] | Others [GC area %] |
|---|---|---|---|---|
| 1 | 93.9 | 0.05 | 4.3 | 1.7 |
| 2 | 94.3 | 0.02 | 4.2 | 0.4 |

GC conditions: 30 m RTX 5 Amine, temperature program: 80° C. start temperature, 8° C./min. heating rate, 280° C. end temperature/15 min. hold time. The H$_2$O content is not taken into account.
*) Amide = gamma-(N-2-pyrrolidinyl)butyramide

We claim:

1. A process for continuously preparing 2-pyrrolidone by reacting gamma-butyrolactone with ammonia in the liquid phase in the presence of water, which comprises carrying out the reaction at a temperature of from 275 to 300° C. and an absolute pressure of from 140 to 180 bar in a molor ratio of the starting materials, gamma-butyrolactone, ammonia and water of 1:(2 to 4):(1 to 3).

2. A process as claimed in claim 1, wherein the reaction is carried out at a temperature of from 280 to 295° C.

3. A process as claimed in claim 1 wherein the reaction is carried out at an absolute pressure of from 150 to 170 bar.

4. A process as claimed in claim 1 wherein the molar ratio of the starting materials, gamma-butyrolactone ammonia and water, is 1:(2.1 to 3:5):(1.5 to 2.8).

5. A process as claimed in claim 1 wherein the reaction is carried out in one stage.

6. A process as claimed in claim 1 wherein the reaction is carried out in a vertical tubular reactor.

7. A process as claimed in claim 1 wherein the reaction is carried out in a liquid phase mode.

8. A process as claimed in claim 6 wherein the gamma-butyrolactone and an ammonia/water-mixture are fed separately to the tubular reactor in the reactor bottom by a two-material injector.

9. A process as claimed in claim 1 wherein the reaction is carried out in the absence of a catalyst.

10. A process as claimed in claim 1 wherein after the first reaction, first excess ammonia, then water and finally the 2-pyrrolidone are distilled out of the reaction product.

11. A process as claimed in claim 1 wherein, after the reaction, first excess ammonia is distilled out of the reaction product in the presence of hydroxides of the metals Na, K, Li, Ba or Ca, in particular in the presence of NaOH.

12. A process as claimed in claim 1 for preparing 2-pyrrolidone having a selectivity of >93%.

13. A process as claimed in claim 1 for preparing 2-pyrrolidone having a purity of >99.5%.

14. A process as claimed in claim 1 for preparing 2-pyrrolidone having an APHA color number ≦30.

* * * * *

UNITED STATES PATENT AND TRADEMARK OFFICE
CERTIFICATE OF CORRECTION

PATENT NO. : 7,164,031 B2  
APPLICATION NO. : 10/487452  
DATED : January 16, 2007  
INVENTOR(S) : Rudloff et al.

Page 1 of 1

It is certified that error appears in the above-identified patent and that said Letters Patent is hereby corrected as shown below:

In column 5, indicated line 27, "gama-butyrolactone ammonia" should read

--gama-butyrolactone, ammonia--

Signed and Sealed this

Eighth Day of April, 2008

JON W. DUDAS  
*Director of the United States Patent and Trademark Office*